United States Patent [19]

Hoffman

[11] Patent Number: 5,165,503
[45] Date of Patent: Nov. 24, 1992

[54] METHOD AND APPARATUS FOR LUBRICATING AND DISINFECTING DENTAL DRILLS

[76] Inventor: Elliott S. Hoffman, 5001 Desert Jewel Dr., Paradise Valley, Ariz. 85253

[21] Appl. No.: 772,060

[22] Filed: Oct. 7, 1991

Related U.S. Application Data

[63] Continuation-in-part of Ser. No. 586,684, Sep. 24, 1990, Pat. No. 5,054,584.

[51] Int. Cl.⁵ .............................. F16N 7/30
[52] U.S. Cl. .................... 184/55.1; 184/105.3; 433/104; 433/114
[58] Field of Search .................. 433/84, 85, 104, 114; 184/6.26, 6.14, 55.1, 55.2, 105.1, 105.3, 6.21

[56] References Cited

U.S. PATENT DOCUMENTS

| | | |
|---|---|---|
| 827,519 | 7/1906 | Emery . |
| 1,388,459 | 8/1921 | C eene et al. . |
| 2,039,177 | 4/1936 | Kenzie .................. 221/47 |
| 2,124,831 | 7/1938 | Roos ..................... 32/28 |
| 2,988,815 | 6/1961 | Staunt .................... 32/27 |
| 3,197,869 | 8/1965 | Staunt .................... 32/26 |
| 3,261,426 | 7/1966 | Kuhlman ................ 184/55 |
| 3,304,051 | 2/1967 | Calhoun ................. 253/3 |
| 3,879,851 | 4/1975 | Landgraf ................ 32/26 |
| 3,946,490 | 3/1976 | Sotman et al. . |
| 3,949,753 | 4/1976 | Dockhorn ............... 433/84 |
| 3,977,083 | 8/1976 | Leslie et al. ............ 32/58 |
| 4,218,216 | 8/1980 | Sugai et al. ............ 433/104 |
| 4,359,317 | 11/1982 | Strohmaier et al. .... 433/85 |
| 4,470,812 | 9/1984 | Martens ................. 433/85 |
| 4,490,113 | 12/1984 | Kawada ................. 433/104 |
| 4,990,087 | 2/1991 | De Rocchis et al. ... 433/104 |

FOREIGN PATENT DOCUMENTS 2526125 4/1982 France .

OTHER PUBLICATIONS

Undated Advertisement for Kisco "Steri-Sleeve".

Primary Examiner—Ira S. Lazarus
Assistant Examiner—Alan B. Cariaso
Attorney, Agent, or Firm—Cahill, Sutton & Thomas

[57] ABSTRACT

A device for disinfecting dental drills having an air turbine motor, or like handpiece, includes a housing having air and water passages extending therein for coupling a flexible supply hose to the handpiece. A first conduit extends from the housing and provides a passageway in fluid communication with the pressurized air inlet passageway of the dental handpiece leading to the air turbine motor. The conduit includes a cap releasably secured to the end of the conduit. The nozzle of a disinfectant reservoir may be inserted within the conduit after temporarily removing the cap for permitting the nozzle to be advanced through the housing and into the handpiece for disinfecting the air passages leading to and from the turbine motor. A second conduit extends from the housing and communicates with the water passage of the housing. The nozzle of the disinfectant reservoir may be inserted into the second conduit, after removing its cap, to disinfect the water passage extending through the dental handpiece. Pressurized air and water may then be passed through the air and water passages, respectively, to remove any remaining disinfectant before using the drill with another patient.

25 Claims, 4 Drawing Sheets

METHOD AND APPARATUS FOR LUBRICATING AND DISINFECTING DENTAL DRILLS

CROSS-REFERENCE TO RELATED APPLICATION

The present application is a continuation-in-part of applicant's co-pending application Ser. No. 07/586,684, filed on Sep. 24, 1990, and entitled "Lubricating Device For Air Driven Dental Drills", which prior application is scheduled to be issued as U.S. Pat. No. 5,054,584 on Oct. 8, 1991.

BACKGROUND OF THE INVENTION

1. Field of the Invention

The present invention relates generally to dental drills, and more particularly, to a method and apparatus for lubricating and disinfecting dental drills or other hand pieces having air turbine motors and which may include a water line for directing a stream of cooling water at a surface being drilled.

2. Description of the Prior Art

Dental drills and similar handpieces often include an air powered turbine head containing a turbine rotor which must be lubricated each day. At present, such daily lubrication requires that the supply hose, which provides pressurized air and water, and in some instances, a source of light, to the dental drill, be uncoupled from the drill so that an elongated, flexible nozzle of a lubricant spray container can be inserted into the air inlet opening of the dental drill that leads to the turbine rotor; the lubricant, typically oil, is then sprayed into the turbine area of the drill. Following lubrication, the supply hose must be reattached to the drill. Reattachment of the supply hose to the dental drill is delicate, taxing, and time-consuming; therefore, personnel assigned the task of lubricating such dental drills often neglect it, and expensive turbines burn out faster than expected.

Those skilled in the art have attempted to solve the problem of easily and effectively lubricating dental drills but have not been entirely successful. U.S. Pat. No. 3,879,851 to Landgraf discloses a device for lubricating dental drills with aerosol spray containers without disassembly of the drills prior to lubrication. The patent to Landgraf discloses an intermediate piece coupled between the turbine head and a hand grip. The intermediate piece includes a port normally sealed by a ball valve whenever the drill is operated. The nozzle of a lubricant container may be introduced into the port when the drill is not in use. However, the nozzle may not be advanced to any significant degree into the drill itself; therefore, the lubricant is not efficiently directed toward the turbine head and can dissipate inside the intermediate piece before reaching the turbine head.

U.S. Pat. No. 3,946,490 to Sotman et al. discloses a device for aerosol lubrication of dental drills. The Sotman device is a specially designed dental handpiece which includes a lubrication opening ordinarily sealed by a sliding clip or collar. A lubrication opening projects angularly into the turbine housing. During lubrication, a tube extending from the discharge port of an aerosol lubricant can is inserted through the lubrication opening; therefore, lubricant can be injected directly from the lubricant can into the turbine housing. However, the Sotman device requires substantial modification to conventional dental drill handpieces which lack such opening.

U.S. Pat. No. 4,218,216 to Sugai et al. discloses a lubrication device inserted between the end of a dental handpiece and the flexible service hose for permitting lubricant to be added to the air supply line. Rather than permitting periodic application of a lubricant from an aerosol spray container, the device disclosed by Sugai et al. continuously adds a mist oil to the compressed air channel. However, such constant lubrication poses a significantly greater risk of inadvertently injecting such lubricant into a patient's mouth as compared with the practice of periodically lubricating a dental handpiece once each day.

In addition, French Patent No. 2526-125 discloses an air motor for a dental handpiece including an air inlet and a separate lubricant branch within the motor body connected to the air inlet passage. The lubricant branch houses a spring loaded, normally closed ball non-return valve. Oil is injected into the lubricant branch, forcing open the ball non-return valve by the pressure of the lubricating device. However, the air motor disclosed within this French patent would require substantial modification of dental handpieces that are already heavily in use.

U.S. Pat. No. 4,490,113 to Kawada discloses a dental handpiece having a rotatable connector for allowing the dental handpiece to be more easily rotated about its axis. The connector includes a radial oiling filler and filler cap for oiling the dental handpiece.

Accordingly, it is an object of the present invention to provide a dental drill lubricating device for periodically lubricating dental drills without requiring disassembly of the dental drill from the associated supply hose.

It is another object of the present invention to provide such a dental drill lubricating device which can be used without modification of the dental handpiece itself.

It is still another object of the present invention to provide a dental drill lubricating device which permits the tip of the lubricant nozzle to be inserted into an air passage within the dental handpiece itself.

High-speed dental handpieces are in common use today because such high-speed handpieces can be used with less discomfort to the dental patient. Such high-speed dental handpieces typically include a water line in addition to pressurized air entry and exhaust lines extending therethrough from the turbine head end of the drill to the opposing hook-up end of the drill that is adapted to mate with the above-described supply hose. The water line terminates in a small nozzle which directs a cooling stream of water at the surface that is being drilled to prevent the build-up of heat which can cause patient discomfort. The control unit operated by the dentist or dental technician (by a foot pedal or otherwise) is adapted to simultaneously start and stop the flow of water each time the drill is operated.

It is believed that each time that the cooling water stream is suddenly shutoff, as when the controlling foot pedal is released, a negative pressure, or back pressure, can develop within the water line of the dental handpiece. It is feared that this negative pressure can actually suction oral fluids from a patient's mouth into the water emitting nozzle of the dental handpiece and into the water line of the handpiece. This potential problem has become of such concern that some cities and municipalities are actually requiring dental offices to install intricate antisyphon devices within their dental offices to prevent any backflow of water being supplied to the dental office from contaminating municipal water supply lines.

Likewise, there is a possibility that negative pressure can develop within the pressurized air inlet and air exhaust lines communicating with the air turbine head of the dental handpiece when the pressurized air supply is released between actuations, and that such negative pressure can similarly suction oral fluids into such lines.

Particularly in view of the recent epidemic of AIDS, dentists and dental technicians have become increasingly aware of the possibility of transmitting diseases from one patient to the next. It is now common for dental technicians to spray a bactericide upon the outer surfaces of dental handpieces and upon the dental chair, as well as to wipe dental drill pieces with alcohol, in order to help prevent the spread of infection from one patient to the next. However, such measures do not effectively neutralize bacteria or viral matter which may have been suctioned into the water and air lines within the dental handpiece itself. While some dental handpieces may be autoclaved to ensure sterility, thousand of dental handpieces are in use which can not be autoclaved because they are incapable of withstanding such high temperatures.

In theory, access to the air inlet, air exhaust, and water lines of the dental handpiece can be obtained by uncoupling the supply hose from the hook-up end of the dental handpiece. However, as noted above, the removal and reattachment of the dental handpiece from the supply hose is a taxing job. If the dental handpiece had to be removed from the supply hose for disinfection purposes between every patient procedure, then the dental office could not attend to as many patients each day.

Accordingly, it is an object of the present invention to provide a dental handpiece disinfection device for allowing the interior passageways of a dental handpiece to be easily and conveniently disinfected between patient procedures without requiring the disassembly of the dental handpiece from its associated supply hose.

It is another object of the present invention to provide such a dental handpiece disinfection device which can be used without modification of the dental handpiece itself.

It is still another object of the present invention to provide such a disinfection device which allows a disinfectant to be introduced into either or both of the pressurized air lines and cooling water line that extend within the dental handpiece.

It is a further object of the present invention which further facilitates the periodic lubrication of the air powered turbine head of the handpiece.

A still further object of the present invention is to provide a convenient method for disinfecting the interior passages of a dental handpiece between successive patient procedures.

Other objects, advantages and features of the present invention will become more apparent to those skilled in the art from the following specification when taken in conjunction with the accompanying drawings.

SUMMARY OF THE INVENTION

Briefly described, and in accordance with preferred embodiments thereof, the present invention relates to a device for disinfection one or more passages of a dental drill handpiece or the like. The device includes a housing having a first end adapted to be connected to the proximal end of the dental handpiece. The housing includes an opposing second end adapted to be coupled to a supply hose. The housing includes one or more passages extending therethrough and providing a fluid connection from the supply hose to corresponding passages of the handpiece for exchanging air and/or water therebetween. The disinfecting device further includes a fastener for releasably fastening the first end of the housing to the proximal end of the dental handpiece.

The disinfecting device further includes a conduit which extends at an angle from the housing. The conduit has a first end secured to the housing in fluid connection with one of the passages extending therethrough. The conduit includes an opposing second end adapted to slidingly receive the flexible nozzle of a disinfectant reservoir, such as an aerosol-charged, or pump-operated container of bactericide. The conduit extends from its second end to its first end generally toward the first end of the housing to convey the nozzle through the associated passage extending within the housing toward the corresponding passage in the dental handpiece. The passageway extending through the conduit forms a Y-junction with the associated passage extending through the housing to guide the tip of the disinfectant reservoir nozzle into the corresponding passage of the dental handpiece.

A cap or other sealing mechanism is releasably secured to the second end of the conduit to seal the opening therein between applications of the disinfectant. For example, the cap may be releasably secured to the second end of the conduit through a threaded coupling.

The aforementioned fastener for releasably fastening the first end of the housing to the proximal end of the dental handpiece preferably includes an internally threaded collar slidably engaged with the distal end of the housing and adapted to threadedly engage the proximal end of the dental handpiece.

In a first embodiment of the present invention, the device is provided in the form of an adapter for insertion between the dental handpiece and the supply hose. The second end of the housing has external threads formed upon the outer periphery thereof for being engaged by a second internally threaded collar slidably engaged with a terminal fitting of the supply hose.

In a second embodiment of the present invention, the housing of the disinfecting device replaces the conventional terminal fitting of the supply hose, wherein the second end of the housing is substantially permanently secured to the grouping of bundled flexible passageways that form the supply hose.

The conduit of the aforementioned disinfection device may be coupled to either the pressurized air inlet passage or the pressurized air exhaust passage of the housing for permitting the introduction of the disinfectant fluid into the pressurized air passages of the dental handpiece without requiring disassembly of the dental handpiece from the supply hose. The disinfectant fluid may thereafter be blown from such passages by resealing the second end of the first conduit and applying pressurized air to the air inlet passage of the dental handpiece. Preferably, the conduit communicates with the air inlet passage of the housing for allowing the same conduit to be used to periodically lubricate the air turbine motor of the dental handpiece.

Alternatively, the conduit of the aforementioned disinfection device may be coupled to the water passage therein for permitting the introduction of the disinfectant fluid into the water passage of the dental handpiece without requiring disassembly of the dental handpiece from the supply hose. The disinfectant fluid may thereafter be flushed from such passage by resealing the second end of the conduit and applying water through the water passage of the housing to rinse out the water passage of the dental handpiece.

Preferably, the disinfection device includes both first and second conduits for allowing the disinfection of both the air lines and the water line.

The present invention also relates to the method of disinfecting interior passages of a dental handpiece by providing a disinfectant reservoir having a thin outlet nozzle for emitting a liquid disinfectant under pressure. The tip of the outlet nozzle is inserted into an interior passage of the dental handpiece, and the liquid disinfectant is applied under pressure to fill such passage with the liquid disinfectant. The outlet nozzle is then removed, and either pressurized air or water is passed through such passage to remove any remaining disinfectant fluid. Preferably, such method is practiced using a housing of the type described above to avoid the need for decoupling the supply hose from the dental handpiece in order to gain access to the interior passages of the dental handpiece.

DESCRIPTION OF THE PREFERRED EMBODIMENTS

Figure 1:
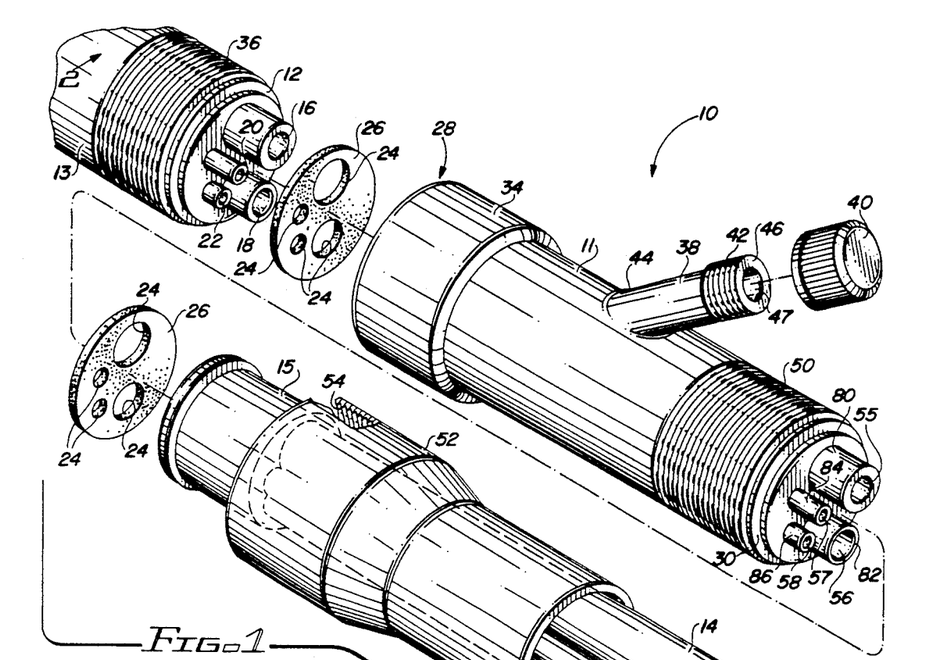
FIG. 1 is an expanded perspective view of a lubrication device for attachment between a dental drill and a dental drill supply hose.

In FIG. 1, a first embodiment of a dental drill lubricating device is indicated generally by reference numeral 10. In this embodiment, device 10 is an intermediary coupler or adapter which can be used to retrofit to existing dental drills and associated supply hoses. Device 10 includes a generally cylindrical housing 11 having a distal end 28 and an opposing proximal end 30. Distal end 28 is adapted to be coupled to proximal end 12 of a handpiece 13 such as a dental drill; the opposing distal end (not shown) of handpiece 13 contains a turbine head including a turbine rotor to drive a tool such as a drill bit (not shown). Proximal end 30 of housing 11 is provided with male threads 50 upon the outer periphery thereof, and is adapted to abut and connect to terminal fitting 15 of supply hose 14. Preferably, the respective couplings of housing 11 to proximal end 12 of handpiece 13 and to terminal fitting 15 of supply hose 14 are sealed by placing one of a pair of rubber gaskets or grommets 26 between the handpiece end 12 and distal end 28 of housing 11, and between the supply hose terminal fitting 15 and proximal end 30 of housing 11.

Figures 2, 3:
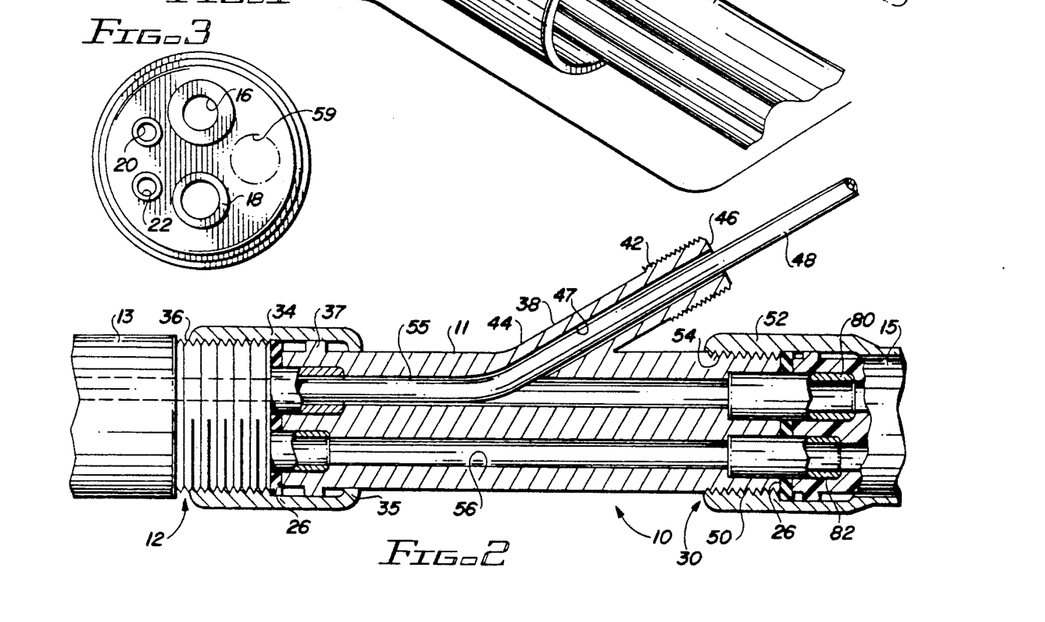
FIG. 2 is a sectional view of the lubrication device shown in FIG. 1 taken on lines 2—2 of FIG. 1.
FIG. 3 is an end view of the lubrication device illustrated in FIGS. 1 and 2.

As shown most clearly in FIG. 3, handpiece end 12 include an enlarged pressurized-air inlet passage 16 and an air outlet passage 18 to circulate compressed, pressurized air from supply hose 14 to the turbine rotor and back; also shown in FIG. 3 is a water inlet passage 20 for admitting water that is directed at the site being drilled to cool the same. Another smaller inlet passage 22 is also shown in FIG. 3 to admit pressurized air which may be directed at the site being drilled to blow away debris. The various air and water inlet and outlet passages are accommodated by corresponding enlarged holes 24 in grommets 26. As shown in FIGS. 1 and 3, housing 11 contains corresponding air inlet and outlet passages 55 and 56, respectively, water inlet passage 57 and pressurized air passage 58; supply hose 14 contains a number of flexible passageways bundled together for conducting the flow of air and water between the handpiece and a source of compressed air and pressurized water. As shown in FIG. 3, an optional fiber optic port or passage 59 may also be included in handpiece 13, within housing 11, and within supply hose 14, to direct a light beam at the work area.

As shown in FIGS. 1 and 2, a plurality of tubular fittings 80, 82, 84, and 86, each communicating with passages 55, 56, 57, and 58, respectively, within housing 11, extend from proximal end 30 of housing 11. Such tubular fittings extend through the corresponding apertures 24 within grommet 26. Tubular fittings 80-86 are received within correspondingly-sized sockets formed in terminal fitting 15 of supply hose 14. Preferably, tubular fittings 80-86 are of the same size and configuration as those extending from the proximal end of handpiece 13, whereby tubular fittings 80-86 readily mate with the sockets conventionally provided within terminal fitting 15. Thus, the proximal end of housing 11 is indistinguishable from the proximal end 12 of handpiece 13.

Referring generally to FIGS. 1 and 2, device 10 further includes a female internally-threaded collar 34 which fits around distal end 28 of housing 11; collar 34 is adapted to slide over distal end 28 of housing 11 and engage male threads 36 provided upon the outer periphery of proximal end 12 of handpiece 13. Before engaging collar 34 with proximal end 12, the air and water passages 16-22 projecting from handpiece 13 are inserted into the corresponding passages provided in the distal end 28 of housing 11. Collar 34 includes an inwardly-turned annular flange 35 adapted to engage an annular boss or ring 37 extending from distal end 28 of housing 11. When collar 34 is thereafter rotated and tightened on male threads 36, the annular flange of collar 34 urges boss 37 toward proximal end 12 of handpiece 13, compressing gasket 26. Device 10 thereby becomes locked to proximal end 12 of handpiece 13, with the various air and water passages of handpiece 13 and housing 11 properly aligned with each other, thus establishing fluid connections therebetween. Collar 34 therefore serves as a means to releasably fasten distal end 28 of housing 11 to proximal end 12 of handpiece 13.

Similarly, terminal fitting 15 of supply hose 14 includes a second slidable collar 52 slidably engaged with terminal fitting 15 and containing female internal threads 54, shown in FIG. 1, to engage male external threads 50 formed upon the outer periphery of proximal end 30 of housing 11. Collar 52 locks the proximal end 30 to terminal fitting 15 of supply hose 14, thus providing a fluid connection between the air and water passages within supply hose 14, and the corresponding air and water passages 55-58 of device 10.

Positioned approximately between distal end 28 and proximal end 30 of housing 11 and extending out at an angle therefrom is a tubular conduit 38. As shown in FIG. 2, first end 44 of conduit 38 is secured to housing 11 and is in fluid communication with air inlet passage 55 of housing 11. The second end 46 of conduit 38 opposite first end 44 has an outer periphery including male threads 42; a female threaded screw-on cap 40 is provided to fit over and releasably engage male threads 42, thus covering and sealing second end 46 of conduit 38 when lubrication is not being performed. As shown in FIG. 2, conduit 38 extends from second end 46 to first end 44 generally toward distal end 28 of housing 11. Conduit 38 provides a lubrication passageway 47 which forms a Y-junction with air inlet passageway 55 of housing 11 and which is adapted to slidingly receive therein a nozzle of a lubricant reservoir.

To lubricate the handpiece or drill 13, cap 40 is removed from second end 46 of conduit 38, and nozzle 48 of an oil spray container (not shown) is inserted into conduit 38 through second end 46 thereof, as shown in FIG. 2. The tip of nozzle 48 is advanced through passageway 47 and through air inlet passage 55 of housing 11, and further into air inlet passage 16 of handpiece 13 toward the vicinity of the turbine rotor (not shown). As shown in FIG. 2, the tip of nozzle 48 lies in a substantially coaxial relationship with air inlet passage 16 of handpiece 13. Oil is then sprayed from the oil container through nozzle 48 and up into the handpiece 13 to lubricate the turbine rotor.

Figure 4:
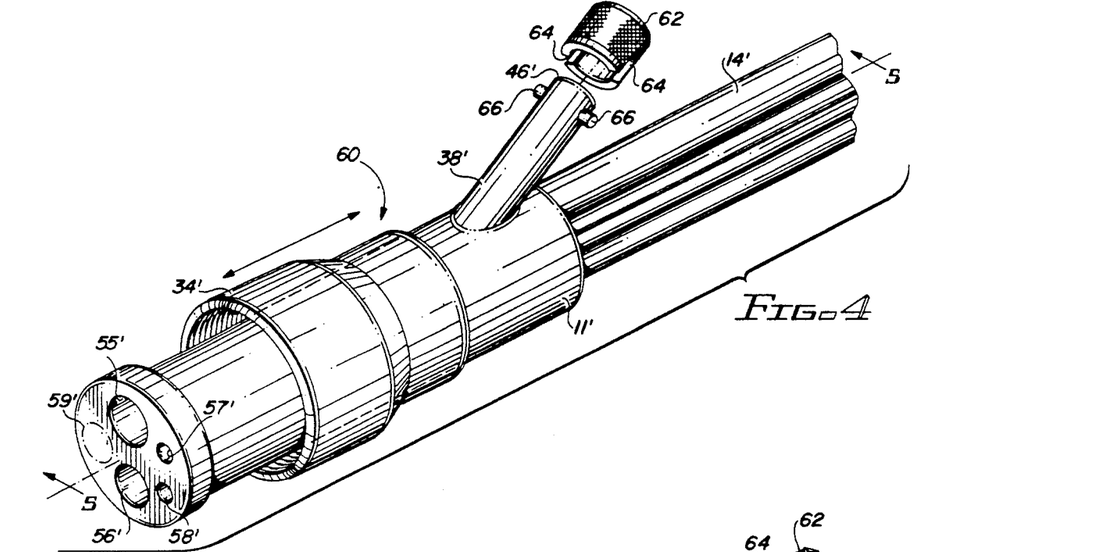
FIG. 4 is a perspective view of a second embodiment of the dental drill lubricating device including modifications to the end of the dental supply hose.
Figure 5:
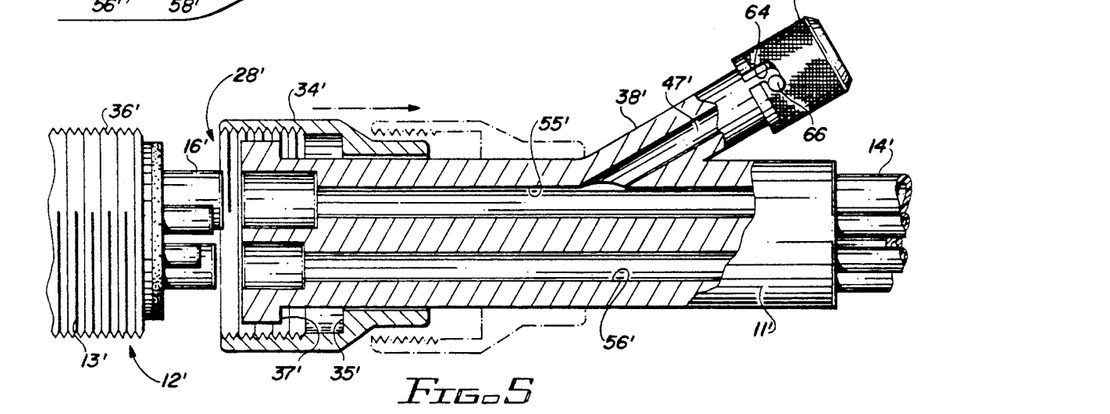
FIG. 5 is a sectional view of the lubrication device shown in FIG. 4 taken on lines 5—5 of FIG. 4.

A second embodiment of the dental drill lubricating device of the present invention is designated generally by reference numeral 60 in FIGS. 4 and 5. This embodiment is intended to be incorporated within newly manufactured supply hoses for dental drills or similar handpieces. Many of the elements of this embodiment are similar to those described with respect to the embodiment illustrated in FIGS. 1-3; therefore, those elements within FIGS. 4 and 5 which correspond with those already identified in FIGS. 1-3 are designated by like reference numerals. The major difference is that device 60 is intended to be permanently connected to supply hose 14', in substitution for terminal fitting 15, thereby eliminating the need for a separate adapter or coupler between supply hose 14' and handpiece 13'. Another difference is that second end 46' of conduit 38' is covered by a bayonet type cap 62 having a pair of opposing L-shaped slots 64 adapted to receive and releasably engage pins 66 extending from the outer surface of conduit 38' adjacent second end 46'. As with the embodiment described with respect to FIGS. 1-3, the nozzle of a spray oil container can be inserted into second end 46' of conduit 38', advanced through lubrication passage 47' of conduit 38' into air inlet passage 55' of housing 11', and thence into the air inlet passage 16' of handpiece 13' toward the air turbine to lubricate the turbine rotor.

Figure 6:
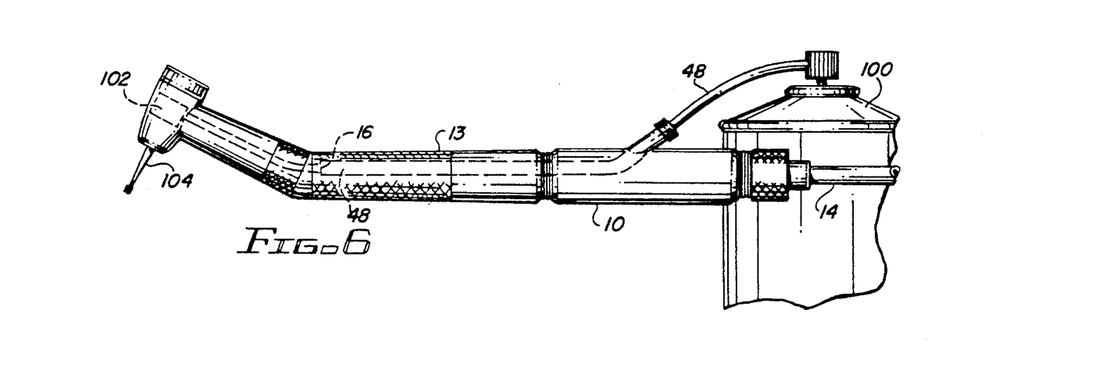
FIG. 6 is a side view of the lubrication device shown in FIG. 1 coupled between a supply hose and a dental handpiece and being used to lubricate the turbine head of the dental handpiece.

Within FIG. 6, lubrication device 10 is shown coupled between dental handpiece 13 and supply hose 14. As shown in FIG. 6, dental handpiece 13 includes a turbine rotor 102 for rotating a tool 104 such as a drill bit. Also shown in FIG. 6 is a lubricant reservoir in the form of an oil spray container 100 having nozzle 48. Nozzle 48 extends within conduit 38, and into air inlet passage 16 of dental handpiece 13.

Figure 7:
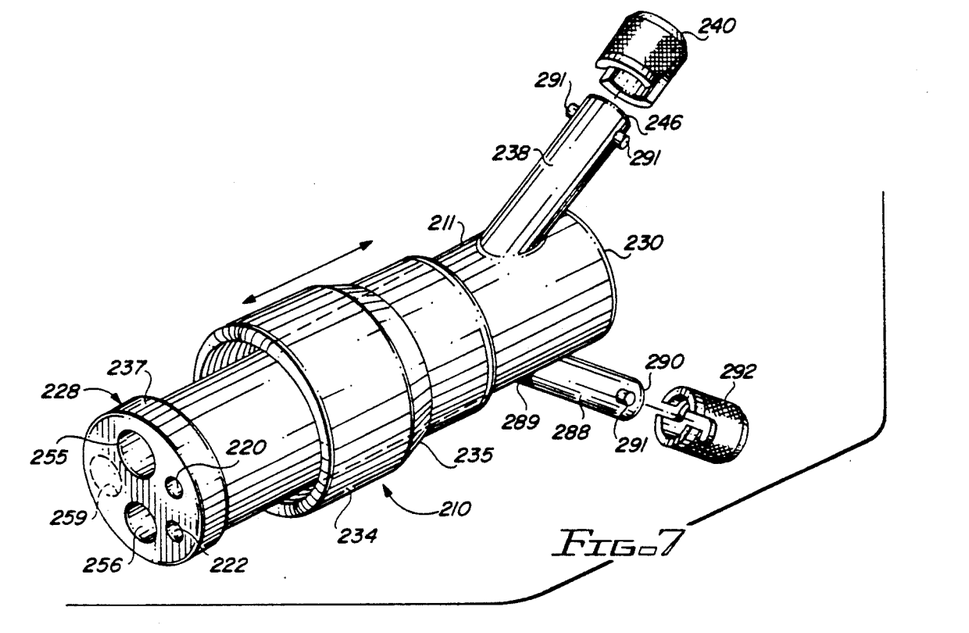
FIG. 7 is a perspective view of a lubrication/disinfection device embodying one form of the present invention for attachment between a dental handpiece and a dental handpiece supply hose.
Figures 8, 10:
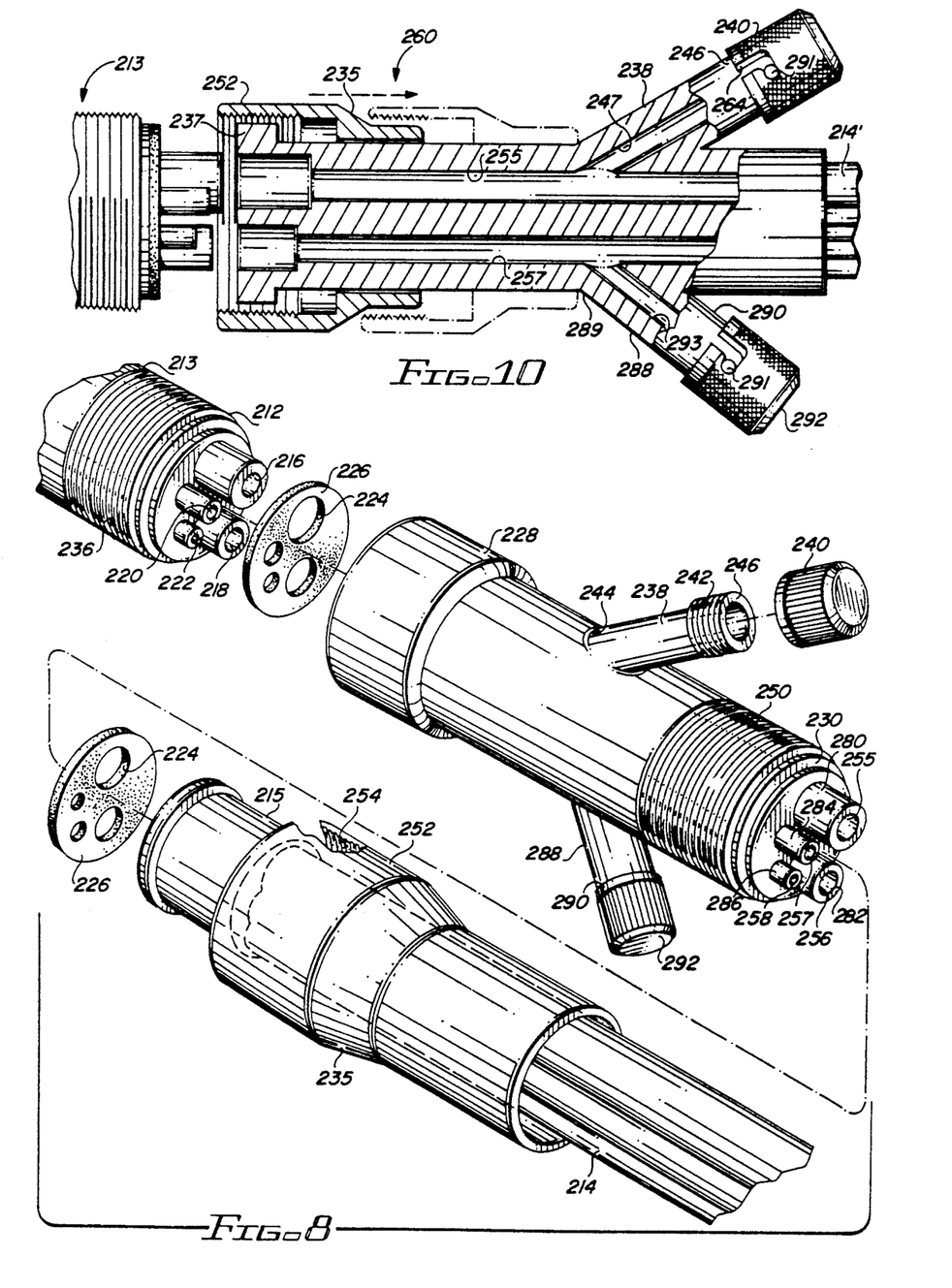
FIG. 8 is an expanded perspective view of the lubrication device shown in FIG. 7 and illustrating the manner by which such device is coupled between a dental handpiece and the dental handpiece supply hose.
FIG. 10 is a sectional view of an alternate embodiment of the present invention wherein the lubrication/disinfection device is incorporated within the hook-up end of the dental supply hose itself.

In FIGS. 7 and 8, a first embodiment of a dental drill disinfecting device is indicated generally by reference numeral 210. In this embodiment, device 210 is an intermediary coupler or adapter which can be used to retrofit to existing dental drills and associated supply hoses. Device 210 includes a generally cylindrical housing 211 having a first end 228 and an opposing second end 230. First end 228 is adapted to be coupled to proximal end 212 of a handpiece 213 such as a dental drill; the opposing distal end 205 (see FIG. 9) of handpiece 213 contains a turbine head 202 including a turbine rotor to drive a tool such as a drill bit 204 (see FIG. 9). Second end 230 of housing 211 is provided with male threads 250 upon the outer periphery thereof, and is adapted to abut and connect to terminal fitting 215 of supply hose 214. Preferably, the respective couplings of housing 211 to proximal end 212 of handpiece 213, and to terminal fitting 215 of supply hose 214, are sealed by placing one of a pair of rubber gaskets or grommets 226 between the handpiece proximal end 212 and the first end 228 of housing 211, and between the supply hose terminal fitting 215 and proximal end 230 of housing 211.

As shown most clearly in FIG. 8, handpiece proximal end 212 includes an enlarged pressurized-air inlet passage 216 and an air outlet passage 218 to circulate compressed, pressurized air from supply hose 214 to the turbine rotor and back; also shown in FIG. 8 is a water inlet passage 220 for admitting water that is directed at the site being drilled to cool the same. Another smaller inlet passage 222 is also shown in FIG. 8 to admit pressurized air which may be directed at the site being drilled to blow away debris. The various air and water inlet and outlet passages are accommodated by corresponding enlarged holes in grommets 226, such as holes 224. As shown in FIGS. 7 and 8, housing 211 contains corresponding air inlet and outlet passages 255 and 256, respectively, water inlet passage 257 and pressurized air passage 258; supply hose 214 contains a number of flexible passageways bundled together for conducting the flow of air and water between the dental handpiece 213 and a source of compressed air and pressurized water. As shown in FIG. 7, an optional fiber optic port or passage 259 may also be included within housing 211, to direct a light beam at the work area.

As shown in FIG. 8, a plurality of tubular fittings 280, 282, 284, and 286, each communicating with passages 255, 256, 257, and 258, respectively, within housing 211, extend from proximal end 230 of housing 211. Such tubular fittings extend through the corresponding apertures 224 within grommet 226. Tubular fittings 280-286 are received within correspondingly-sized sockets formed in terminal fitting 215 of supply hose 214. Preferably, tubular fittings 280-286 are of the same size and configuration as those extending from the proximal end of dental handpiece 213, whereby tubular fittings 280-286 readily mate with the sockets conventionally provided within terminal fitting 215. Thus, the second end of housing 211 is indistinguishable from the proximal end 212 of dental handpiece 213.

Referring generally to FIGS. 7 and 8, device 210 further includes a female internally-threaded collar 234 which fits around distal end 228 of housing 211; collar 234 is adapted to slide over distal end 228 of housing 211 and engage male threads 236 provided upon the outer periphery of proximal end 212 of dental handpiece 213. Before engaging collar 234 with proximal end 212, the air and water passages 216-222 projecting from handpiece 213 are inserted into the corresponding passages provided in the distal end 228 of housing 211. Collar 234 includes an inwardly-turned annular flange 235 adapted to engage an annular boss or ring 237 extending from first end 228 of housing 211. When collar 234 is thereafter rotated and tightened on male threads 236, the annular flange of collar 234 urges boss 237 toward proximal end 212 of handpiece 213, compressing gasket 226. Device 210 thereby becomes locked to proximal end 212 of handpiece 213, with the various air and water passages of handpiece 213 and housing 211 properly aligned with each other, thus establishing fluid connections therebetween. Collar 234 therefore serves as a means to releasably fasten first end 228 of housing 211 to proximal end 212 of handpiece 213.

Similarly, terminal fitting 215 of supply hose 214 includes a second slidable collar 252 slidably engaged with terminal fitting 215 and containing female internal threads 254, shown in FIG. 1, to engage male external threads 250 formed upon the outer periphery of second end 230 of housing 211. Collar 252 locks the second end 230 to terminal fitting 215 of supply hose 214, thus providing a fluid connection between the air and water passages within supply hose 214, and the corresponding air and water passages 255-258 of device 210.

Positioned approximately between first end 228 and second end 230 of housing 211 and extending out at an angle therefrom is a first tubular conduit 238. As shown in FIGS. 7 and 8, first end 244 of first conduit 238 is secured to housing 211 and is in fluid communication with air inlet passage 255 of housing 211. The second end 246 of conduit 238 opposite first end 244 has an outer periphery including male threads 242; a female threaded screw-on cap 240 is provided to fit over and releasably engage male threads 242, thus covering and sealing second end 246 of conduit 238 when disinfection is not being performed. As shown in FIGS. 7 and 8, conduit 238 extends from second end 246 to first end 244 generally toward distal end 228 of housing 211. Conduit 238 provides a disinfectant passageway 247 (See FIG. 10) which forms a Y-junction with air inlet passageway 255 of housing 211 and which is adapted to slidingly receive therein a flexible outlet nozzle 248 of a disinfectant reservoir (see FIG. 9).

Figure 9:
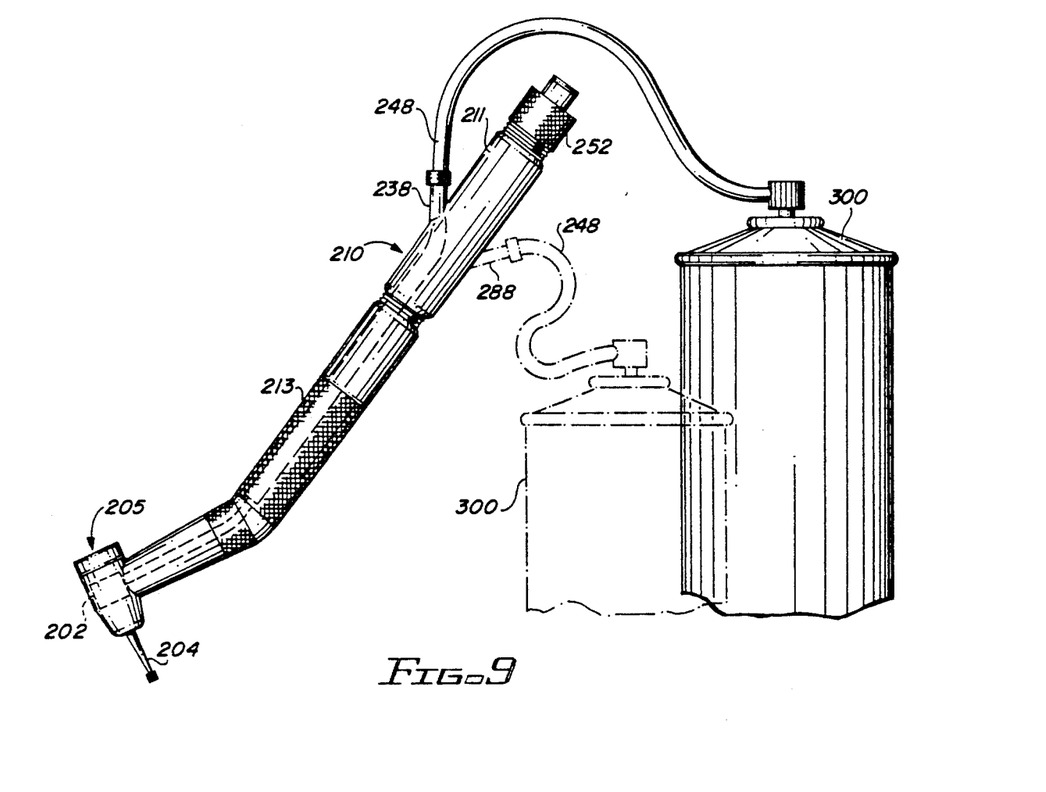
FIG. 9 is a front view of a dental handpiece equipped with the lubrication/disinfection device of FIG. 7 and illustrating the manner by which the tip of a flexible nozzle of a spray can containing lubricant or disinfectant may be inserted into either the pressurized air inlet line or cooling water line of the dental handpiece.

To disinfect the pressurized air passages 216 and 218 of dental handpiece 213, cap 240 is removed from second end 246 of conduit 238, and nozzle 248 of disinfectant spray container 300 is inserted into conduit 238 through second end 246 thereof, as shown in FIG. 9. The tip of nozzle 248 is advanced through passageway 247 and through air inlet passage 255 of housing 211, and further into air inlet passage 216 of handpiece 213 toward the distal end 205 thereof. A disinfectant liquid is then sprayed from the disinfectant container 300 through nozzle 248 and into the handpiece 213 to disinfect air passages 216 and 218 of dental handpiece 213.

The preferred disinfectant liquid solution for use in disinfecting the interior passages of the dental handpiece is a 2% solution of glutaraldehyde, such as the product commercially available from Metrex Research Corporation of Parker, Colo. under the brand name "METRICIDE", identified by Product No. MX-1400. This product is an activated dialdehyde solution used for sterilization and disinfection. Such product is sporicidal, virucidal, fungicidal, tuberculocidal, bactericidal, and pseudomonacidal, and is recommended for use in sterilizing medical instruments, such as lensed instruments, respiratory therapy equipment, thermometers, endoscopes, and sharp instruments. The product is recommended for use in hospitals, dental offices, nursing homes, and health care institutions. Directions for use advise the user to cleanse and rinse the lumens of any hollow instruments before filling with solution.

Within FIG. 9, the disinfectant reservoir is shown in the form of a pressurized aerosol container 300 having a flexible elongated outlet nozzle 248. Reservoir 300 could also be in the form of a non-pressurized plastic spray bottle having a hand-operated pump with a finger-actuated trigger for squirting disinfectant fluid through nozzle 248.

Still referring to FIGS. 7 and 8, a second tubular conduit 288 is shown extending from housing 211 and extending out at an angle therefrom. The first end 289 of second conduit 288 is secured to housing 211 and is in fluid communication with water passage 257 of housing 211. The second end 290 of second conduit 288 may either be externally threaded like conduit 238 in FIG. 8, or include bayonet pins like those shown in FIG. 7, for mating with a removable sealing cap 292 in order to seal second end 290 of second conduit 288 when disinfection is not being performed. As shown in FIGS. 7, 8, and 9, second conduit 288 extends from second end 290 generally toward first end 228 of housing 211. Second conduit 288 provides a disinfection passageway 293 (see FIG. 10) which forms a Y-junction with water passage 257 of housing 211 and which is adapted to slidingly receive therein flexible outlet nozzle 248 of disinfectant reservoir 300.

To disinfect the water passage 220 of dental handpiece 213, cap 292 is removed from second end 290 of second conduit 288, and nozzle 248 is inserted into conduit 288 of housing 211, as shown in dashed outline in FIG. 9. The tip of nozzle 248 is advanced through passageway 293 and through water passage 257 of housing 211, and further into water passage 220 of dental handpiece 213 directed toward the distal end 205 thereof. The disinfectant liquid is then sprayed from container 300 through nozzle 248 and into the handpiece 213 to disinfect water passage 220 thereof. Water from supply hose 214 may then be circulated through housing 211 and into water passage 220 of dental handpiece 213 to flush the disinfectant solution therefrom. If desired, cap 292 may be left off during a portion of this flushing process to flush passageway 293 of any remaining disinfectant fluid. Cap 292 is thereafter resecured before the dental handpiece is used to perform a procedure on another patient.

A second embodiment of the dental drill disinfecting device of the present invention is designated generally by reference numeral 260 in FIG. 10. This embodiment is intended to be incorporated within newly manufactured supply hoses for dental drills or similar handpieces. Many of the elements of this embodiment are similar to those described with respect to the embodiment illustrated in FIGS. 7 and 8; therefore, those elements within FIG. 10 which correspond with those already identified in FIGS. 7 and 8 are designated by like reference numerals. The major difference is that device 260 is intended to be permanently connected to supply hose 214', in substitution for terminal fitting 215, thereby eliminating the need for a separate adapter or coupler between supply hose 214' and handpiece 213. As in FIG. 7, the second end 246 of conduit 238 is covered by a bayonet type cap 240 having a pair of opposing L-shaped slots 264 adapted to receive and releasably engage pins 291 extending from the outer surface of conduit 238 adjacent second end 246.

As with the embodiment described with respect to FIGS. 7 and 8, nozzle 248 of disinfectant spray container 300 can be inserted into second end 246 of first conduit 238 of housing 260 shown in FIG. 10, advanced through passage 247 of conduit 238 into air inlet passage 255 of housing 260, and thence into the air inlet passage 216 of handpiece 213 toward the air turbine to disinfect the air passages of the dental handpiece 213. Similarly, the nozzle of a lubricant reservoir, like that shown in FIG. 6, may also be inserted within passageway 247 to periodically lubricate the turbine rotor.

As with the embodiment described in FIGS. 7 and 8, nozzle 248 of disinfectant spray container 300 can be inserted into second end 290 of second conduit 288 of housing 260 shown in FIG. 10, advanced through passageway 293, into water passage 257 of housing 260, and thence into the water passage 220 of dental handpiece 213 toward the distal end thereof to disinfect the water passage of dental handpiece 213.

Those skilled in the art will now appreciate that a device has been described which permits a dentist or dental technician to easily and conveniently disinfect the interior air and water passages of a dental handpiece. Moreover, such disinfection device does not require the need to uncouple the dental handpiece from its associated supply hose each time disinfection is to be performed. Such device simultaneously facilitates the periodic lubrication of the air turbine rotor. Those skilled in the art will also appreciate that an improved method for disinfecting the interior passages of a dental handpiece has also been described. While the present invention has been described in accordance with preferred embodiments thereof, the description is for illustrative purposes only and should not be construed as limiting the scope of the invention. Various changes and modifications may be made by those skilled in the art without departing from the true spirit and scope of the invention as defined by the appended claims.

I claim:

1. A device for disinfecting an air exchange passage of a dental drill handpiece or the like, the handpiece having an air driven turbine rotor proximate a distal end thereof for rotating a tool and having a proximal end providing at least an air exchange passage for conveying pressurized air between the turbine rotor and a supply hose, said device comprising in combination:
    a) a housing having a first end adapted to be connected to the proximal end of the handpiece, and having an opposing second end adapted to be coupled to a supply hose, the housing having at least an air exchange passage extending therethrough and providing a fluid connection from the supply hose to the air exchange passage of the handpiece;
    b) fastening means for releasably fastening the first end of said housing to the proximal end of the handpiece;
    c) a conduit extending at an angle from said housing, said conduit having a first end secured to said housing between the first and second ends of said housing, the first end of said conduit being in fluid connection with the air exchange passage of said housing, said conduit having an opposing second end adapted to slidingly receive therein a nozzle of a disinfectant reservoir;
    d) a cap releasably secured to the second end of said conduit to seal the second end of said conduit when the dental handpiece is in use; and
    e) said conduit being generally directed toward the first end of said housing to convey the nozzle through the housing toward the turbine rotor, whereby disinfectant can be supplied from the disinfectant reservoir through the nozzle toward the turbine rotor for disinfecting the air exchange passage.

2. A device as recited by claim 1 wherein the proximal end of the handpiece includes external threads upon the outer periphery thereof, said fastening means including an internally threaded collar slidably engaged with the first end of said housing and adapted to threadedly engage the externally threaded proximal end of the handpiece to releasably secure the first end of said housing to the proximal end of the handpiece, with the air exchange passage of the handpiece and the air exchange passage of said housing being in fluid communication with each other.

3. A device as recited by claim 2 wherein the supply hose terminates in a fitting having at least an air exchange passage therein and including a second collar slidably engaged with the terminal fitting, the second collar being internally threaded, and the second end of said housing having external threads formed upon the outer periphery thereof for being engaged by the second collar for joining the second end of said housing with the terminal fitting of the supply hose.

4. A device as recited by claim 1 wherein the second end of said conduit is threaded, and wherein said cap is also threaded to releasably engage the second end of said conduit.

5. The device as recited by claim 1 wherein the supply hose includes a plurality of bundled flexible passageways for conducting the flow of air and water, and wherein said housing includes a corresponding plurality of passageways for conducting the flow of air and water between the supply hose and the handpiece.

6. The device as recited by claim 5 wherein the second end of said housing is substantially permanently secured to the supply hose.

7. A device as recited by claim 3 wherein a plurality of tubular fittings extend from the second end of said housing, said tubular fittings being in fluid communication with a corresponding plurality of passageways within said housing, said device further including a grommet having apertures formed therein, the apertures corresponding in size and number to the plurality of tubular fittings extending from the second end of said housing, said plurality tubular fittings extending through the corresponding apertures of said grommet, and said grommet sealing the second end of said housing to the terminal fitting of the supply hose.

8. A device as recited by claim 1 wherein said conduit includes a disinfection passageway in fluid communication with the air exchange passage of said housing, said disinfection passageway forming a Y-junction with the air exchange passage provided within said housing.

9. A device as recited by claim 1 wherein the air exchange passage of said housing to which said conduit connects supplies pressurized air to an air inlet passage of the dental handpiece.

10. The device recited by claim 1 wherein the second end of said conduit is adapted to slidingly receive a nozzle of a lubricant reservoir for periodically applying a lubricant to the air driven turbine rotor of the dental handpiece.

11. A device as recited by claim 1 wherein the air exchange passage of said housing to which said conduit connects exhausts pressurized air from an air exhaust passage of the dental handpiece.

12. A device for disinfecting a water passage of a dental drill handpiece or the like, the handpiece having an air driven turbine rotor proximate a distal end thereof for rotating a tool, the handpiece further including a water nozzle for directing a stream of water at the surface upon which the tool is operating, the handpiece having a proximal end providing at least a water passage for conveying water from a supply hose to the water nozzle, said device comprising in combination:
   a) a housing having a first end adapted to be connected to the proximal end of the handpiece, and having an opposing second end adapted to be coupled to a supply hose, the housing having at least a water passage extending therethrough and providing a fluid connection from the supply hose to the water passage of the handpiece;
   b) fastening means for releasably fastening the first end of said housing to the proximal end of the handpiece;
   c) a conduit extending at an angle from said housing, said conduit having a first end secured to said housing between the first and second ends of said housing, the first end of said conduit being in fluid connection with the water passage of said housing, said conduit having an opposing second end adapted to slidingly receive therein a nozzle of a disinfectant reservoir;
   d) a cap releasably secured to the second end of said conduit to seal the second end of said conduit when the dental handpiece is in use; and
   e) said conduit being generally directed toward the first end of said housing to convey the reservoir nozzle through the housing toward the distal end of the dental handpiece, whereby disinfectant can be supplied from the disinfectant reservoir through the reservoir nozzle toward the distal end of the dental handpiece for disinfecting the water passage thereof.

13. A device as recited by claim 12 wherein the proximal end of the handpiece includes external threads upon the outer periphery thereof, said fastening means including an internally threaded collar slidably engaged with the first end of said housing and adapted to threadedly engage the externally threaded proximal end of the handpiece to releasably secure the first end of said housing to the proximal end of the handpiece, with the water passage of the handpiece and the water passage of said housing being in fluid communication with each other.

14. A device as recited by claim 13 wherein the supply hose terminates in a fitting having at least a water passage therein and including a second collar slidably engaged with the terminal fitting, the second collar being internally threaded, and the second end of said housing having external threads formed upon the outer periphery thereof for being engaged by the second collar for joining the second end of said housing with the terminal fitting of the supply hose.

15. A device as recited by claim 12 wherein the second end of said conduit is threaded, and wherein said cap is also threaded to releasably engage the second end of said conduit.

16. The device as recited by claim 12 wherein the supply hose includes a plurality of bundled flexible passageways for conducting the flow of air and water, and wherein said housing includes a corresponding plurality of passageways for conducting the flow of air and water between the supply hose and the dental handpiece.

17. The device as recited by claim 16 wherein the second end of said housing is substantially permanently secured to the supply hose.

18. A device as recited by claim 14 wherein a plurality of tubular fittings extend from the second end of said housing, said tubular fittings being in fluid communication with a corresponding plurality of passageways within said housing, said device further including a grommet having apertures formed therein, the apertures corresponding in size and number to the plurality of tubular fittings extending from the second end of said housing, said plurality of tubular fittings extending through the corresponding apertures of said grommet, and said grommet sealing the second end of said housing to the terminal fitting of the supply hose.

19. A device as recited by claim 12 wherein said conduit includes a disinfection passageway in fluid communication with the water passage of said housing, said disinfection passageway forming a Y-junction with the water passage provided within said housing.

20. A method for disinfecting interior passages of a dental handpiece or the like between patient procedures, the dental handpiece having an air driven turbine rotor proximate a distal end thereof for rotating a tool and having a proximal end providing at least an air exchange passage for conveying pressurized air between the turbine rotor and a supply hose, the supply hose being coupled to the proximal end of the dental handpiece, said method comprising the steps of:
   a. providing a disinfectant reservoir having a thin flexible outlet nozzle for emitting a liquid disinfectant under pressure, the nozzle having a tip;
   b. inserting the tip of the outlet nozzle of the disinfectant reservoir into the air exchange passage of the dental handpiece while maintaining the supply hose coupled to the proximal end of the dental handpiece;
   c. applying the liquid disinfectant under pressure through the nozzle into the air exchange passage for filling such passage with liquid disinfectant;
   d. removing the outlet nozzle from the air exchange passage of the dental handpiece; and
   e. applying pressurized air from the supply hose to the air exchange passage for blowing therefrom any remaining liquid disinfectant.

21. The method recited by claim 20 wherein the air exchange passage of the dental handpiece is an air inlet passage for receiving pressurized air to rotate the turbine rotor.

22. The method recited by claim 20 wherein the air exchange passage of the dental handpiece is an air exhaust passage for discharging pressurized air from the turbine rotor.

23. The method recited by claim 20 further including the steps of:
  a. interposing a housing between a proximal end of the dental handpiece and the supply hose, the housing having at least an air exchange passage extending therethrough for providing a fluid connection from the supply hose to the air exchange passage of the handpiece, the housing further including a conduit extending at an angle from the housing, the conduit having a first end secured to the housing between first and second ends of the housing and being generally directed toward the first end of the housing, a first end of the conduit being in fluid connection with the air exchange passage of the housing;
  b. fastening the first end of the housing to the proximal end of the handpiece;
  c. fastening the second end of the housing to the supply hose;
  d. inserting the outlet nozzle of the disinfectant reservoir into the second end of the conduit to convey the tip of the outlet nozzle through the housing toward the turbine rotor for supplying disinfectant from the disinfectant reservoir through the outlet nozzle toward the turbine rotor for disinfecting the air exchange passage of the dental handpiece;
  e. removing the outlet nozzle from the conduit; and
  f. sealing the second end of the conduit after removing the outlet nozzle therefrom.

24. A method for disinfecting interior passages of a dental handpiece or the like between patient procedures, the dental handpiece having an air driven turbine rotor proximate a distal end thereof for rotating a tool, the dental handpiece further including a water nozzle for directing a stream of water at the surface upon which the tool is operating, the dental handpiece having a proximal end providing at least a water passage for conveying water from a supply hose to the water nozzle, the supply hose being coupled to the proximal end of the dental handpiece, said method comprising the steps of:
  a. providing a disinfectant reservoir having a thin flexible outlet nozzle for emitting a liquid disinfectant under pressure, the nozzle having a tip;
  b. inserting the tip of the outlet nozzle of the disinfectant reservoir into the water passage of the dental handpiece while maintaining the supply hose coupled to the proximal end of the dental handpiece;
  c. applying the liquid disinfectant under pressure through the nozzle into the water passage for filling such passage with liquid disinfectant;
  d. removing the outlet nozzle form the water passage of the dental handpiece; and
  e. applying water from the supply hose to the water passage for flushing therefrom any remaining liquid disinfectant.

25. The method recited claim 24 further including the steps of:
  a. interposing a housing between a proximal end of the dental handpiece and the supply hose, the housing having at least a water passage extending therethrough for providing a fluid connection from the supply hose to the water passage of the dental handpiece, the housing further including a conduit extending at an angle from the housing, the conduit having a first end and an opposing second end, the first end of the conduit being secured to the housing between first and second ends of the housing and being generally directed toward the first end of the housing, the first end of the conduit being in fluid connection with the water passage of the housing;
  b. fastening the first end of the housing to the proximal end of the dental handpiece;
  c. fastening the second end of the housing to the supply hose;
  d. inserting the outlet nozzle of the disinfectant reservoir into the second end of the conduit to convey the tip of the outlet nozzle through the housing toward the water passage of the dental handpiece for supplying disinfectant from the disinfectant reservoir through the outlet nozzle and into the water passage of the dental handpiece for disinfecting the air water passage of the dental handpiece;
  e. removing the outlet nozzle from the conduit; and
  f. sealing the second end of the conduit after removing the outlet nozzle therefrom.

* * * * *